United States Patent [19]

Urano et al.

[11] Patent Number: 4,935,413
[45] Date of Patent: Jun. 19, 1990

[54] CARBAMATE PHYSICAL PROPERTY-IMPROVING REAGENT

[75] Inventors: Satoshi Urano; Ryuzo Mizuguchi, both of Yawata; Noriyuki Tsuboniwa, Higashiosaka; Kei Aoki, Ikoma; Yuji Suzuki, Suita; Takeyasu Itoh, Toyo, all of Japan

[73] Assignee: Nippon Paint Co., Ltd., Osaka, Japan

[21] Appl. No.: 58,782

[22] Filed: Jun. 5, 1987

Related U.S. Application Data

[63] Continuation of Ser. No. 751,698, Jul. 2, 1985, abandoned.

[30] Foreign Application Priority Data

| Jul. 3, 1984 | [JP] | Japan | 59-138298 |
| Jul. 3, 1984 | [JP] | Japan | 59-138299 |
| Aug. 23, 1984 | [JP] | Japan | 59-138300 |
| Aug. 23, 1984 | [JP] | Japan | 59-176176 |
| Sep. 14, 1984 | [JP] | Japan | 59-193424 |
| May 27, 1985 | [JP] | Japan | 60-114481 |
| May 28, 1985 | [JP] | Japan | 60-117304 |
| May 28, 1985 | [JP] | Japan | 60-177305 |
| May 28, 1985 | [JP] | Japan | 60-117313 |
| May 28, 1985 | [JP] | Japan | 60-117303 |

[51] Int. Cl.$^5$ ............ C07C 125/04; C07C 125/06; C07D 303/08; C07D 207/12; C07D 209/02; C07D 211/36; C07D 451/02; C07D 265/30

[52] U.S. Cl. ............ 514/178; 560/137; 560/163; 560/157; 514/489; 514/490; 514/478; 514/476; 514/304; 514/315; 514/424; 514/428; 514/594; 514/183; 514/241; 514/230.8; 514/237.8; 549/553; 549/334; 544/168; 544/216; 558/233; 564/46; 552/544

[58] Field of Search ............ 560/137, 163, 157; 514/489, 490, 478, 178, 476, 304, 234, 315, 424, 428, 594, 183, 241, 230.8, 237, 8; 260/397.2; 549/553, 334; 548/550, 567, 966; 546/242, 247, 127; 544/168, 216; 558/233; 564/46

[56] References Cited

U.S. PATENT DOCUMENTS 3,337,600 8/1967 Speziale et al. ............ 558/233
3,551,159 12/1970 Froehlich ............ 560/137

FOREIGN PATENT DOCUMENTS 23976 7/1980 European Pat. Off. ............ 560/163
14767 2/1981 European Pat. Off. ............ 560/163
827553 12/1951 Fed. Rep. of Germany ...... 560/163
888769 7/1953 Fed. Rep. of Germany ...... 560/137
2644820 4/1988 Fed. Rep. of Germany ...... 560/137

OTHER PUBLICATIONS

Chemical Abstracts, vol. 82, No. 8, Feb. 24, 1975, p. 124, Abstract No. 45278f (Dainippon Toryo Co., Ltd.).
Chemical Abstracts, vol. 72, No. 19, May 11, 1970, p. 324, Abstract No. 100246q (H. Diefenbach).
The Journal of Organic Chemistry, vol. 28, No. 3, Mar. 22, 1963, pp. 875–876 (C. D. Gutsche).
Chemical Abstracts, vol. 98, No. 13, Mar. 29, 1983, p. 641, Abstract No. 107732r (H. R. Kricheldorf) & Chemical Substance Index, p. 5754CS.
Chem. Ber., vol. 84, pp. 4–12 (1951) (Th. Lieser et al.).
Die Makromoleculare Chemie, vol. 131, pp. 247–257 (1970).
JP-B1-27802/1970 (BASF Aktiengesellschaft) German Pat. Appln. No. P 16 43 723.3, filed 12/27/67.
JP-B1-18135/1970 (BASF Aktiengesellschaft) German Pat. Appln. No. P 16 43 730.2 filed 12/30/67.
Journal of Paint Technology, vol. 39, pp. 104–117 (1967).
Solvents Theory and Practice, pp. 1–3, 132–135, 168–169 and 175–179 (1973).
Paint/Coatings Dictionary, p. 391 (1978).

Primary Examiner—Mary C. Lee
Assistant Examiner—Robert C. Whittenbaugh
Attorney, Agent, or Firm—Wegner & Bretschneider

[57] ABSTRACT

A physical property-improving reagent which comprises an alkenoylcarbamate compound of the formula:

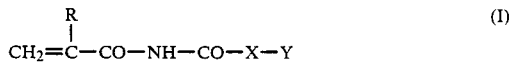

wherein R is a hydrogen atom or a lower alkyl group, X is an oxygen atom (—O—), a sulfur atom (—S—) or a substituted or unsubstituted imino group (—NR'—), R' being a hydrogen atom or a lower alkyl group, and Y is the residue of an active hydrogen atom-containing compound excluding —X-H therefrom dissolved in an organic solvent having a solubility parameter of not less than 8, which can impact excellent physical properties to a polymer produced with the same.

20 Claims, No Drawings

CARBAMATE PHYSICAL PROPERTY-IMPROVING REAGENT

This application is a continuation of Ser. No. 751,698, filed July 2, 1985 now abandoned.

The present invention relates to a physical property-improving reagent. More particularly, it relates to a monomeric reagent which can be readily polymerized by itself or with any other ethylenically unsaturated compound(s) to impart excellent physical properties to the resultant polymer.

In recent years, a great number of polymers are artificially produced and used in various fields. With development of polymers, there are always demands to new polymers having better, enhanced or improved physical properties.

As a result of the extensive study seeking new polymers having excellent physical properties such as high elasticity, good adhesion and favorable dispersibility, it has now been found that when the following alkenoylcarbamate compounds are incorporated into polymer chains, the resultant polymer chains show remarkable enhancement in physical properties, particularly in elasticity, adhesion and dispersibility:

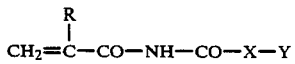
(I)

wherein R is a hydrogen atom or a lower alkyl group, X is an oxygen atom (—O—), a sulfur atom (—S—) or a substituted or unsubstituted imino group (—NR′—), R′ being a hydrogen atom or a lower alkyl group, and Y is the residue of an active hydrogen atom-containing compound excluding —X—H therefrom.

Throughout the specification, the term "lower" used in connection with alkyl, alkenyl, alkynyl, etc. is intended to mean a group having not more than 8 carbon atoms, particularly not more than 5 carbon atoms. For instance, examples of lower alkyl are methyl, ethyl, n-propyl, isopropyl, n-butyl, isobutyl, t-butyl, n-pentyl, isopentyl, etc. Y is the residue of an active hydrogen atom-containing compound such as an alcohol, a thiol, a carboxylic acid, a thiocarboxylic acid, ammonia, a primary amine, a secondary amine or an amide excluding —X—H therefrom. Accordingly, specific examples of Y are alkyl, alkenyl, alkynyl, aryl, aralkyl, acyl, thioacyl, etc. If necessary, R′ and Y may be bonded together to make a divalent chain such as alkylene, alkenylene or alkynylene. In general, these monovalent or divalent groups and chains have a molecular weight of not more than 1,000, particularly not more than 500, more particularly not more than 300.

The alkenoylcarbamate compounds (I) have a highly active ethylenic unsaturation and can be readily polymerized by themselves or with any other ethylenically unsaturated compounds. They are usually available in a stable solid form under the atmospheric condition and can be dissolved easily in various solvents, particularly those having a solubility parameter of not less than 8, so that their handling is quite easy and their polymerization can be made in solution with ease.

In addition to the high reactivity due to the ethylenic unsaturation, the acylurethane structure in the alkenoylcarbamate compounds (I) contributes in enhancement of cohesion. Thus, the polymers incorporated with the alkenoylcarbamate compounds (I) as the monomeric units can show various advantageous properties such as high elasticity, good adhesion and favorable dispersibility due to the improved cohesion. Further, the alkenoylcarbamate compounds (I) can be provided with various characteristic properties by introducing a certain specific group or structure into the opposite end to the ethylenic unsaturation. For instance, the introduction of an epoxy or aziridino group affords the alkenoylcarbamate compounds (I) having a reactive site due to the epoxy or aziridino group in addition to the one due to the ethylenic unsaturation. Also, the introduction of a blocked isocyanate structure provides the alkenoylbarcamate compounds (I) with the latent reactivity due to an isocyanate group, which will be actualized from the blocked isocyanate structure under cetain conditions. Moreover, various other functional groups or structures may be introduced into the alkenoylcarbmate compounds (I) at the opposite end to the ethylenic unsaturation so that the functional properties attributed to said functional groups or structures are imparted to the alkenoylcarbamate compounds (I) and the polymers manufactured therewith. Examples of such functional groups or structures are fluorine-containing groups, melamine-containing structures, non-contractive structures, photosensitive groups, etc.

As the examples of the alkenoylcarbamate compounds (I), there are included the following compounds:

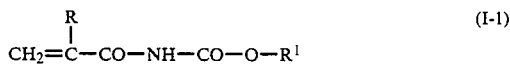
(I-1)

wherein R is as defined above and $R^1$ is the residue of a hydroxyl group-containing compound excluding a hydroxyl group therefrom such as alkyl (e.g. methyl, ethyl, propyl, stearyl), alkenyl (e.g. allyl, pentenyl), aralkyl (e.g. benzyl, phenethyl), substituted cr unsubstituted phenyl (e.g. phenyl, tolyl, xylyl, chlorophenyl, bromophenyl, nitrophenyl) or cholesteryl, particularly alkyl having not more than 20 carbon atoms, lower alkenyl, phenyl(lower)-alkyl, phenyl or cholesteryl;

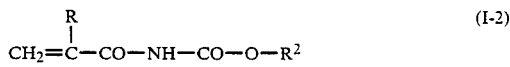
(I-2)

wherein R is as defined above and $R^2$ is the residue of a hydroxyl group-containing compound having an epoxy group excluding a hydroxyl group therefrom such as glycidyl or glycidyloxy(lower)alkyl;

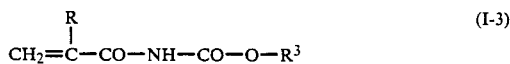
(I-3)

wherein R is as defined above and $R^3$ is the residue of a hydroxyl group-containing compound having a tertiary amino group excluding a hydroxyl group therefrom such as di(lower)alkylamino(lower)alkyl (e.g. dimethylaminomethyl, dimethylaminoethyl, dimethylaminopropyl, diethylaminoethyl, diethylaminopropyl, N-methyl-N-ethylaminopropyl), di(lower)-alkylaminophenyl (e.g. o-dimethylaminophenyl, m-diaminophenyl, p-dimethylaminophenyl, m-diethylaminophenyl), lower alkyl-phenylamino(lower)alkyl (e.g. N-methyl-N-phenylaminoethyl, N-methyl-N-phenylaminopropyl), lower alkylphenyl(lower)alkylamino(lower)alkyl (e.g. N-methyl-N-benzylaminoethyl, N-ethyl-N-benzylaminoethyl, N-ethyl-N-phenethylaminopropyl), pyrrolidino, piperidino, morpholino, pyrrolidino(lower)alkyl (e.g. pyrrolidinoethyl, pyrrolidinopropyl), piperidino(lower)alkyl (e.g. piperidinoethyl, piperidinopropyl), morpholino(lower)alkyl (e.g. morpholinoethyl, morpholinopropyl), di(lower)alkylamino(lower)alkoxy(lower)-alkyl (e.g. dimethylaminoethoxyethyl, dimethylaminoethoxypropyl, diethylaminoethoxypropyl) or 2-(8-methyl-8-azabicyclo[3.2.1]oct-3-yloxycarbonyl)-2-phenylethyl;

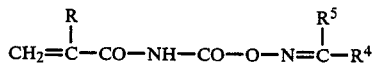  (I-4)

wherein R is as defined above and

is the residue of a carbonyl compound excluding an oxo group therefrom, $R^4$ and $R^5$ being each hydrogen, alkyl (e.g. methyl, ethyl, propyl, stearyl), alkenyl (e.g. allyl, pentenyl), aralkyl (e.g. benzyl, phenethyl), substituted or unsubstituted phenyl (e.g. phenyl, tolyl, xylyl, chlorophenyl, bromophenyl, nitrophenyl) or alkanoyl (e.g acetyl), or $R^4$ and $R^5$ being taken together to form an alkylene chain (e.g. tetramethylene, pentamethylene), particularly $R^4$ and $R^5$ being each hydrogen, alkyl having not more than 20 carbon atoms, phenyl or lower alkanoyl, or $R^4$ and $R^5$ being taken together to form a lower alkylene chain;

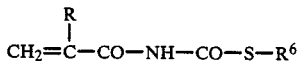  (I-5)

wherein R is as defined above and $R^6$ is the residue of a thiol compound excluding a thiol group therefrom such as alkyl (e.g. methyl, ethyl, propyl, stearyl), cycloalkyl (e.g. cyclopentyl, cyclohexyl), alkenyl (e.g allyl, pentenyl), aralkyl (e.g benzyl, phenethyl) or substituted or unsubstituted phenyl or naphthyl (e.g. phenyl, naphthyl, tolyl, xylyl, chlorophenyl, bromophenyl, nitrophenyl), particularly alkyl having not more than 20 carbon atoms, cyclo(lower)alkyl, lower alkenyl, phenyl(lower)alkyl, phenyl or naphthyl;

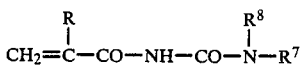  (I-6)

wherein R is as defined above and

is the residue of ammonia, a primary amine or a secondary amine excluding a hydrogen atom therefrom, $R^7$ and $R^8$ being each hydrogen, alkyl (e.g. methyl, ethyl, propyl, stearyl), cycloalkyl (e.g. cyclopentyl, cyclohexyl), alkenyl (e.g. allyl, pentenyl), aralkyl (e.g. benzyl, phenethyl), substituted or unsubstituted phenyl (e.g. phenyl, tolyl, xylyl, chlorophenyl, bromophenyl, nitrophenyl), substituted or unsubstituted heterocycle (e.g. thiazolyl, oxazolyl, isoxazolyl) or the like, or $R^7$ and $R^8$ being taken together with the nitrogen atom to which they are attached to form a substituted or unsubstituted nitrogen atom-containing heterocycle (e.g. aziridino, pyrrolidino, piperidino, morpholino, thiamorpholino, N-methylpiperazino), particularly $R^7$ and $R^8$ being each hydrogen, alkyl having not more than 20 carbon atoms, cyclo(lower)alkyl, lower alkenyl, phenyl(lower)alkyl, phenyl or thiazolyl, or $R^7$ and $R^8$ being taken together with the nitrogen atom to which they are attached to form a morpholino group;

  (I-7)

wherein R is as defined above, $R^9$ is a hydrogen atom or a hydrocarbon group such as alkyl (e.g. methyl, ethyl, propyl, isopropyl, n-butyl, t-butyl, lauryl, stearyl), alkenyl (e.g. allyl, butenyl), aryl (e.g. phenyl, naphthyl) or aralkyl (e.g. benzyl, phenethyl) and $R^{10}$ is a hydrogen atom, or $R^9$ and $R^{10}$ are taken together to form a hydrocarbon chain such as alkylene (e.g. trimethylene, pentamethylene) or alkenylene, particularly $R^9$ is hydrogen, alkyl having not more than 20 carbon atoms, lower alkenyl, phenyl or phenyl(lower)alkyl and $R^{10}$ is hydrogen, or $R^9$ and $R^{10}$ are taken together to form a lower alkylene group;

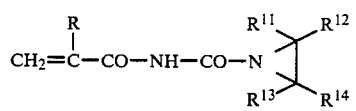  (I-8)

wherein R is as defined above and $R^{11}$, $R^{12}$, $R^{13}$ and $R^{14}$ are each hydrogen or lower alkyl (e.g. methyl, ethyl, n-propyl, isopropyl, n-butyl, sec-butyl), etc.

Other examples of the alkenoylcarbamate compound (I) are as follows:

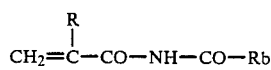  (I-9)

wherein R is as defined above and Rb is the residue of a blocking agent excluding an active hydrogen atom therefrom;

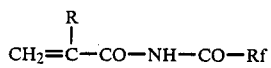  (I-10)

wherein R is as defined above and Rf is the residue of a fluorine atom-containing compound excluding an active hydrogen atom therefrom;

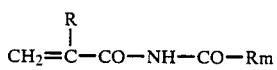  (I-11)

wherein R is as defined above and Rm is the residue of a triazine skeleton-containing compound excluding an active hydrogen atom therefrom;

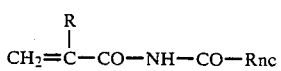  (I-12)

wherein R is as defined above and Rnc is the residue of a non-contractive structure-containing compound excluding an active hydrogen atom therefrom;

$$CH_2=\overset{R}{\underset{|}{C}}-CO-NH-CO-Rp \quad (I-13)$$

wherein R is as defined above and Rp is the residue of a photosensitive group-containing compound excluding an active hydrogen atom therefrom, etc.

The alkenoylcarbamate compounds (I) can be usually produced by reacting an alkenoylisocyanate of the formula:

$$CH_2=\overset{R}{\underset{|}{C}}-CO-NCO \quad (II)$$

wherein R is as defined above with an active hydrogen atom-containing compound of the formula:

$$H-X-Y \quad (III)$$

wherein X and Y are each as defined above.

The alkenoylisocyanate (II) is known (Chem. Ber., 84, 4 (1951)) and can be advantageously produced, for instance, by reacting the corresponding amide of the formula:

$$CH_2=\overset{R}{\underset{|}{C}}-CONH_2$$

wherein R is as defined above with an oxalyl halide (e.g. oxalyl chloride) in an inert solvent such as a halogenated hydrocarbon (e.g. carbon tetrachloride, chloroform, dichloromethane, dichloroethane, trichloroethane) at a temperature of −30° to 100° C., optionally followed by reacting the intermediate of the formula:

$$X'CH_2-\overset{R}{\underset{|}{CH}}-CO-NCO \quad (IV)$$

wherein R is as defined above and X' is a halogen atom (e.g. chlorine) with a hydrogen halide-eliminating agent in an inert solvent such as a hydrocarbon (e.g. benzene, toluene, hexane) or a halogenated hydrocarbon (e.g. carbon tetrachloride, chloroform) at a temperature of 0° to 150° C.

As the hydrogen halide-eliminating agent, there may be used not only a hydrogen halide-eliminating agent in a strict sense, i.e. the one to be used theoretically in at least an equimolar amount to the haloalkanoyl isocyanate (IV), but also a hydrogen halide-eliminating catalyst, which may be employed in an amount smaller than the equimolar amount. Specific examples of the hydrogen halide-eliminating agent are amines such as triethylamine, 1,8-diazabicyclo[5.4.0]undecene-7, pyridine and quinoline, alkali metal or alkaline earth metal hydroxides such as sodium hydroxide, potassium hydroxide and magnesium hydroxide, metal oxides such as copper oxide, magnesium oxide, calcium oxide, alumina and iron oxide, metal complexes such as $(Ph_3P)_2Ru(CO)_3$ and $(PhP)_3Pt$ (wherein Ph is phenyl), metal halides such as lithium chloride, titanium chloride, aluminum chloride and sodium chloride, metal salts such as zinc naphthenate, nickel acetate, barium sulfate and potassium phosphate, metal alkoxides such as potassium t-butoxide, sodium ethoxide and sodium isopropoxide, synthetic zeolites such as molecular sieve and microporous glass, boric acid, oxirane, metal zinc, triphenyl phosphine, etc. Among them, particularly preferred are those chosen from amines, metal oxides, metal halides, synthetic zeolites, triphenyl phosphine, etc.

As the active hydrogen atom-containing compound (III), there may be used alcohols, thiols, carboxylic acids, thiocarboxylic acids, ammonia, primary amines, secondary amines, amides, etc. Specific examples are those of the following formulas: $R^1-OH$ (wherein $R^1$ is as defined above), $R^2-OH$ (wherein $R^2$ is as defined above), $R^3-OH$ (wherein $R^3$ is as defined above), $R^4R^5C=N-OH$ (wherein $R^4$ and $R^5$ are each as defined above), $R^6-SH$ (wherein $R^6$ is as defined above), (wherein $R^7R^8N-H$ (wherein $R^7$ and $R^8$ are each as defined above), $R^9-CO-NHR^{10}$ (wherein $R^9$ and $R^{10}$ are each as defined above), $$\overset{R^{11}}{\underset{R^{13}}{\diagdown}}\overset{R^{12}}{\underset{R^{14}}{\diagup}}N-H$$

(wherein $R^{11}$, $R^{12}$, $R^{13}$ and $R^{14}$ are each as defined above), Rb-H (wherein Rb is as defined above), Rf-H (wherein Rf is as defined-above), Rm-H (wherein Rm is as defined above), Rnc-H (wherein Rnc is as defined above), Rp-H (wherein Rp is as defined above), etc.

More specifically, the one chosen from the following compounds may be used as the active hydrogen atom-containing compound (III):

Hydroxyl group-containing compounds such as alkanols (e.g. methanol, ethanol, n-propanol, isopropanol, n-butanol, t-butanol, stearyl alcohol), alkenols (e.g. allyl alcohol), aralkanols (e.g. benzyl alcohol, phenethyl alcohol), phenol and cholesterol;

Epoxy group-containing compounds having a hydroxyl group such as glycidol and glycidyloxyalkanols (e.g. 2-glycidyloxyethanol);

Tertiary amino group-containing compounds having a hydroxyl group such as dialkylaminoalkanols (e.g. dimethylaminomethanol, dimethylaminoethanol, dimethylaminopropanol, diethylaminoethanol, diethylaminopropanol, N-methyl-N-ethylaminopropanol), dialkylaminophenols (e.g. o-dimethylaminophenol, m-dimethylaminophenol, p-dimethylaminophenol, m-diethylaminophenol), alkylphenylaminoalkanols (e.g. N-methyl-N-phenylaminoethanol, N-methyl-N-phenylaminopropanol), alkylphenylalkylaminoalkanols (e.g. N-methyl-N-benzylaminoethanol, N-ethyl-N-benzylaminoethanol, N-ethyl-N-phenethylaminopropanol), N-hydroxypyrrolidine, N-hydroxypiperidine, N-hydroxymorpholine, pyrrolidinoalkanols (e.g. pyrrolidinoethanol, pyrrolidinopropanol), piperidinoalkanols (e.g. piperidinoethanol, piperidinopropanol), morpholinoalkanols (e.g. morpholinoethanol, morpholinopropanol), dialkylaminoalkoxyalkanols (e.g. dimethylaminoethoxyethanol, dimethylaminoethoxypropanol, diethylaminoethoxypropanol) and atropine;

Oximes such as alkanealdehyde oximes (e.g. acetaldehyde oxime), alkenealdehyde oximes, aralkanealdehyde oximes, phenylaldehyde oximes, dialkylketone oximes (e.g. acetone oxime, methylethylketone oxime, methylisobutylketone oxime), dialkenylketone oximes, alkylalkenylketone oximes, phenylalkylketone oximes (e.g. phenylmethylketone oxime), lower alkanoylacetone oximes (e.g. acetylacetone oxime) and cycloalkanone oximes (e.g. cyclopentanone oxime, cyclohexanone oxime);

Thiol compounds such as alkanethiols (e.g. methanethiol, ethanethiol, stearylmercaptan), cycloalkanethiols (e.g. cyclohexanethiol), alkenethiols (e.g. allylmercaptan), aralkanethiols (e.g. benzylmercaptan), thiophenol and thionaphthol;

Ammonia, primary amines and secondary amines such as ammonia, alkylamines (e.g. methylamine, ethylamine, propylamine, isopropylamine, laurylamine, stearylamine), alkenylamines (e.g. allylamine, pentenylamine), aralkylamines (e.g. benzylamine, phenethylamine), aniline, thiazolylamine, dialkylamines (e.g. dimethylamine, methylethylamine, diethylamine, dipropylamine), dicycloalkylamines (e.g. dicyclopentylamine, dicyclohexaylamine), alkylaralkylamines (e.g. methyl-benzylamine, methyl-phenethylamine) and cyclic amines (e.g. piperidine, morpholine, aziridine);

Amides such as formamide, acetamide, propionamide, butyramide, laurylamide, stearylamide, benzamide, phenylacetamide, phenylpropionamide, alpha-methyleneacetamide, pyrrolidone, piperidone and epsilon-caprolactam;

Aziridines such as alkyleneimines (e.g. ethyleneimine, propyleneimine), etc.

Other examples of the active hydrogen atom-containing compound (III) are as follows:

Blocking agents as conventionally employed for blocking an isocyanate group such as alkanols (e.g. methanol, ethanol, chloroethanol, propanol, t-butanol, pentanol, 2-methyl-1-butanol, hexanol, heptanol, octanol, nonanol, 3,3,5-trimethylhexanol, 2-ethylhexanol, decyl alcohol), aralkanols (e.g. benzyl alcohol, phenethyl alcohol, methylbenzyl alcohol), etherified alcohols (e.g. ethylene glycol monoethyl ether, ethylene glycol monobutyl ether, 1-methoxy-2-propanol), aromatic alcohols (e.g. phenol, cresol, 2,6-di-t-butyl-p-cresol, xylenol, nitrophenyl, chlorophenol, ethylphenol, t-butylphenol, methyl p-hydroxybenzoate), active methylene compounds (e.g. acetylacetone, diethyl malonate), lactams (e.g. propionlactam, butyrlactam, valerolactam, epsilon-caprolactam), N-hydroxyimides (e.g. N-hydroxyphthalimide, N-hydroxysuccinimide), oximes (e.g. acetaldoxime, methylethylketone oxime, acetone oxime, cyclohexanone oxime), imidazoles (e.g. 1,3-imidazole), triazoles (e.g. 1,2,3-benzotriazole) and amines (e.g. dicyclohexylamine);

Fluorine atom-containing compounds such as 1,1,1,3,3,3-hexafluoroisopropanol, o-aminobenzotrifluoride, m-aminobenzotrifluoride, p-aminobenzotrifluoride, 2-amino-5-bromobenzotrifluoride, 3-amino-4-bromobenzotrifluoride, 5-amino-2-bromobenzotrifluoride, 2-amino-5-chlorobenzotrifluoride, 3-amino-4-chlorobenzotrifluoride, 5-amino-2-chlorobenzotrifluoride, 2-amino-5-fluorobenzotrifluoride, 3-amino-4-fluorobenzotrifluoride, 5-amino-2-fluorobenzotrifluoride, 3-amino-5-methoxybenzotrifluoride, 2-amino-5-nitrobenzotrifluoride, 4-amino-3-nitrobenzotrifluoride, 5-amino-2-nitrobenzotrifluoride, 4-amino-2,3,5,6-tetrafluorobenzamide, 4-amino-2,3,5,6-tetrafluorobenzoic acid, 4-amino-2,3,5,6-tetrafluorobenzonitrile, bis(trifluoromethylacetamide), chlorodifluoroacetamide, chlorodifluoroacetic acid, 3-chloro-4-fluoroaniline, 2-chloro-6-fluorobenzoic acid, 3-chloro-4-fluorobenzoic acid, 2-chloro-6-fluorobenzyl alcohol, 2-chloro-4-fluorophenol, 2-chloro-6-fluorophenylacetic acid, 1-chloro-3-fluoro-2-propanol, 4-chloro-3-hydroxybenzotrifluoride, decafluorobenzhydrol, 3,4-diaminobenzotrifluoride, 3,5-diaminobenzotrifluoride, 4,4'-diaminooctafluorobiphenyl, 1,3-dichlorotetrafluoroisopropanol, difluoroacetic acid, 2,4-difluoroaniline, 2,5-difluoroaniline, 2,6-difluoroaniline, 2,4-difluorobenzamide, 2,5-difluorobenzamide, 2,6-difluorobenzamide, 3,4-difluorobenzamide, 2,4-difluorobenzoic acid, 2,5-difluorobenzoic acid, 2,6-difluorobenzoic acid, 3,4-difluorobenzoic acid and 1H,1H-pentadecafluorooctanol;

Triazine skeleton-containing compounds such as melamine, methylolated melamines (e.g. monomethylolated melamine, dimethylolated melamine, trimethylolated melamine, tetramethylolated melamine, pentamethylolated melamine, hexamethylolated melamine), lower alkoxymethylolmelamines (e.g. methoxymethylolmelamine, ethoxymethylolmelamine, propoxymethylolmelamine, butoxymethylolmelamine) and guanamines (e.g. formoguanamine, acetoguanamine, benzoguanamine, phenylacetoguanamine, methoxyguanamine);

Non-contractive structure-containing compounds such as those of the formulas:

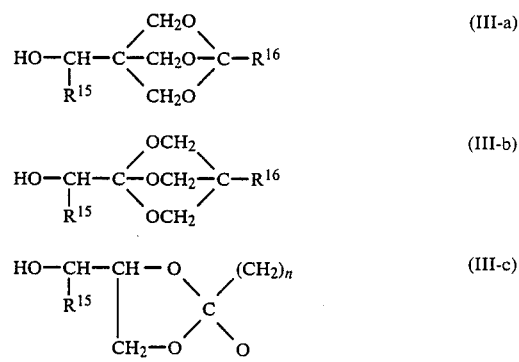

wherein $R^{15}$ and $R^{16}$ are each hydrogen or lower alkyl (e.g. methyl, ethyl, propyl) and n is an integer of 3 to 5, more specifically 1-methyl-4-hydroxymethyl-2,6,7-trioxabicyclo[2.2.2]octane, 1-ethyl-4-hydroxymethyl-2,6,7-trioxabicyclo[2.2.2]octane, 4-ethyl-1-hydroxymethyl-2,6,7-trioxabicyclo[2.2.2]octane, 2-hydroxymethyl-1,4,6-trioxaspiro[4.4]nonane, 2-hydroxymethyl-1,4,6-trioxaspiro[4.5]decane, 2-hydroxymethyl-1,4,6-trioxaspiro[4.6]undecane, 4-methyl-1-(alphahydroxyethyl)-2,6,7-trioxabicyclo[2.2.2]octane, 4-ethyl-1-(alpha-hydroxyethyl)-2,6,7-trioxabicyclo[2.2.2]octane, etc.;

Photosensitive group-containing compounds, i.e. compounds having a photosensitive group or structure such as olefin, cinnamoyl, cinnamylidene, cinnamylideneacetyl, furylacryloyl, coumarine, pyron, benzalacetophenone, styrilpyridine, anthracene, stilben, alpha-phenylaleimide, azide, phenylazide, sulfonylazide, carbonylazide, diazo, alpha-quinonediazide, benzophenone, benzoin, 1,3-dioxane, dithiocarbamate, xanthete, 1,2,3-thiadiazole, cyclopropene, azadioxabicyclo and spiropyran, more specifically benzoin, acetoin, p-hydroxybenzaldehyde, p-hydroxybenzophenone, 1,4,9,10-tetrahydroxyanthracene, benzohydrol, ascorbic acid, cinnamyl alcohol, benzylic acid, 4-methoxyphenol, p-nitrophenol, 2-mercaptobenzothiazole, p-aminoacetophenone, thiocyanamine, alcohols, thiols, carboxylic acids, thiocarboxylic acid and amines derived from benzophenone, acetophenone, 9- fluoresoneacetophenone, alpha-benzoylbenzoic acid, benzylphenylketone, propiophenone, benzalacetophenone, benzoylacetone, benzaldehyde and the like, etc.

In general, the reaction between the alkenoylisocyanate (II) and the active hydrogen atom-containing compound (III) may be carried out at a temperature of −20° to 100° C., particularly at room temperature (0° to 30° C.) or while cooling with ice. The use of an inert solvent as the reaction medium is not essential but preferable in most cases. Examples of the inert solvent are hydrocarbons (e.g. pentane, hexane, heptane, benzene, toluene, xylene, cyclohexane, methylcyclohexane, decalin, petroleum ether, petroleum benzin), halogenated hydrocarbons (e.g. carbon tetrachloride, chloroform, 1,2-dichloroethane), ethers (e.g. diethyl ether, ethyl isopropyl ether, dioxane, tetrahydrofuran), ketones (e.g. acetone, methyl ethyl ketone, methyl isobutyl ketone, cyclohexanone, acetophenone, isophorone), esters (e.g. ethyl acetate, butyl acetate), acetonitrile, dimethylformamide, dimethylsulfoxide. etc.

Depending upon the kind of the active hydrogen atom-containing compound (III), some variations may be made in the reaction conditions so as to carry out the reaction smoothly or achieve the reaction with better results. For instance, when the active hydrogen atom-containing compound (III) is the one of the formulas: $R^1$—OH, $R^2$—OH or $R^3$—OH, a tin catalyst may be present in the reaction system.

Alternatively, the alkenoylcarbamate compounds (I) can be produced by reacting the haloalkanoylisocyanate of the formula:

wherein R and X' are each as defined above with the active hydrogen atom-containing compound (III), optionally in an inert solvent, at a temperature of −20° to 100° C. (particularly at room temperature or while cooling wich ice), followed by reacting the resulting intermediate of the formula:

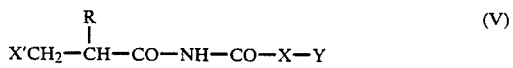

wherein R, X, X' and Y are each as defined above with an hydrogen halide-eliminating agent, optionally in an inert solvent, at a temperature of 0° to 150° C.

The reaction between the haloalkanoylisocyanate (IV) and the active hydrogen atom-containing compound (III) may be carried out substantially in the same manner as in that between the alkenoylisocyanate (II) and the active hydrogen atom-containing compound (III). The inert solvent as optionally usable therein may be the one as exemplified above. The reaction between the intermediate (V) and the hydrogen halide-eliminating agent may be also carried out substantially in the same manner as in that between the intermediate (IV) and the hydrogen halide-eliminating agent. The hydrogen halide-eliminating agent and the inert solvent usable therein are those as exemplified above.

Recovery of the reaction product from the reaction mixture may be accomplished by a per se conventional separation procedure such as evaporation of the solvent under admospheric or reduced pressure.

During the reaction and/or the post-treatment, a small amount of a polymerization inhibitor may be incorporated into the reaction system or the reaction mixture for prevention of the unnecessary polymerization on the ethylenic unsaturation. Examples of the polymerization inhibitor are hydroqyinone, p-methoxyphenol, 2,6-di-t-butyl-4-methylphenol, 4-t-butylcatechol, bisdihydroxybenzylbenzene, 2,2'-methylene-bis(6-t-butyl-3-merhylphenol), 4,4'-butylidene-bis(6-t-butyl-3-methylphenol), 4,4'-thio-bis(6-t-butyl-3-methylphenol), p-nitrosophenol, diisopropylxanthogenesulfide, N-nitrosophenylhydroxylamine ammonium salt, 1,1-diphenyl-2-picrylhydrazil, 1,3,5-tri-phenylpheldazyl, 2,6-di-t-butyl-alpha-(3,5-di-t-butyl-4-oxo-2,5-cyclohexadien-1-ylidene)-p-trioxy, 2,2,6,6-tetramethyl-4-piperidone-1-oxil, dithiobenzoyl sulfide, p,p'-ditolyl trisulfide, p,p'-ditolyl tetrasulfide, dibenzyl tetrasulfide, tetraethylthiuram disulfide, etc.

As stated above, the alkenoylcarbamate compounds (I) have a double bond and are polymerizable by themselves or with various ethylenically unsaturated double bond-containing monomers with ease. Since the alkenoylcarbamate compounds (I) are usually in a solid state and sufficiently stable in the atmosphere. Further, they are readily soluble in various solvents and can be handled in the form of solution. Thus, the polymerization with the alkenoylcarbamate compounds (I) is advantageously effected by the use of their solutions according to a per se conventional mode of solution polymerization. For the polymerization, the use of a radical catalyst such as azobisisobutyronitrile is favorable.

As the solvent for the alkenoylcarbamate compounds (I), there is preferably used the one having a solubility parameter of not less than 8. Specific examples of such solvent are aliphatic and alicyclic hydrocarbons (e.g. cyclohexane, dipentene), aromatic hydrocarbons (e.g. ethylbenzene, toluene, xylene, benzene, tetralin), halogenated hydrocarbons (e.g. carbon tetrachloride, 1,2-dichloropropane, chloroform, chlorobenzene, methylene chloride, ethylene dichloride, o-dichlorobenzene), nitrated hydrocarbons (e.g. nitrobenzene, nitromethane, nitroethane), ethers (e.g. dimethyl ether, dioxane, tetrahydrofuran), alcohol ethers (e.g. butyl carbitol, butyl cellosolve, methyl cellosolve), esters (e.g. ethyl acetate, butyl acetate, cellosolve acetate, methyl acetate, ethylene carbonate, ethyl lactate, propyl formate), ketones (e.g. methyl isobutyl ketone, acetone, isophorone, diacetone alcohol, methylcyclohexanone, cyclohexanone, cyclopentanone), alcohols (e.g. diethylene glycol, 2-ethylhexanol, t-butanol, n-hexanol, n-butanol, cyclohexanol, isopropanol, n-propanol, benzyl alcohol, ethanol, methanol), acetonitrile, N,N-dimethylformamide, dimethylsulfoxide, styrene, methyl methacrylate, ethyl acrylate, n-butyl acrylate, isobutyl methacrylate, n-butyl methacrylate, 2-hydroxyethyl acrylate, 2-hydroxyethyl methacrylate, methacrylic acid, acrylic acid, acrylonitrile, etc.

The solutions of the alkenoylisocyanate compounds (I) in these solvents may be used as the reagents for improvement of physical properties, because they can be reacted with various compounds by the aid of the ethylenic unsaturation therein and impart advantageous properties such as high elasticity, good adhesion and favorable dispersibility to the resulting products. These properties are particularly useful for resins to be used in coating compositions.

The reaction with the alkenoylisocyanate compound (I) may be carried out according to a per se conventional procedure. In case of the polymerization, for instance, a monomeric mixture comprising the alkenoylisocyanate compound (I) optionally with any other ethylenically unsaturated compound(s) in an inert solvent may be subjected to solution polymerization in the presence of a conventional radical polymerization catalyst such as azobisisobutyronitrile or t-butylperoxy-2-ethylhexanoate.

Practical and presently preferred embodiments of the invention are illustratively shown in the following Examples wherein part(s) and % are by weight unless otherwise indicated. The viscosity is the value obtained by measurement at 25° C. with a viscometer Model E (manufactured by Tokyo Keiki K.K.) unless otherwise stated.

Example 1

A solution of methacryloyl isocyanate (11.1 g; 0.1 mol) in 1,2-dichloroethane (50 ml) was dropwise added to dry methanol (32 g; 1 mol) under nitrogen stream while cooling with ice. After completion of the addition, methanol and 1,2-dichloroethane were evaporated under reduced pressure. The residue (14.16 g) was recrystallized from a mixture of hexane and benzene to give methyl N-methacryloylcarbamate (13.15 g) as colorless needles. M.P., 94°–95° C.

Example 2

A solution of methacryloyl isocyanate (11.1 g; 0.1 mol) in 1,2-dichloroethane (50 ml) was dropise added to dry benzyl alcohol (10.8 g; 0.1 mol) under nitrogen stream while cooling with ice. After completion of the addition, 1,2-dichloroethane was evaporated under reduced pressure. The residue (21.8 g) was recrystallized from a mixture of hexane and benzene to give benzyl N-methacryloylcarbamate as colorless needles. M.P., 109°–110° C.

Example 3

A solution of methacryloyl isocyanate (11.1 g; 0.1 mol) in 1,2-dichloroethane (50 ml) was dropise added to a solution of dry phenol (9.4 g; 0.1 mol) in chloroform (20 ml) under nitrogen stream while cooling with ice. After completion of the addition, chloroform and 1,2-dichloroethane were evaporated under reduced pressure. The residue (20.5 g) was recrystallized from a mixture of hexane and benzene to give phenyl N-methacryloylcarbamate as colorless needles. M.P., 94°–95° C.

Examples 4 to 16

In the same manner as in Example 1, the following compounds were produced:

Methyl N-acryloylcarbamate, colorless needles; M.P., 139°–140° C.;
Ethyl N-acryloylcarbamate, colorless needles; M.P., 77°–78° C.;
Phenyl N-acryloylcarbamate, colorless needles; M.P., 135°–136° C.;
Benzyl N-acryloylcarbamate, colorless needles; M.P., 98°–99° C.;
Allyl N-acryloylcarbamate, colorless needles; M.P., 54°–55° C.;
Cholesteryl N-acryloylcarbamate, colorless needles; M.P., 117°–119° C.;
Ethyl N-methacryloylcarbamate, colorless needles; M.P., 73°–74° C.;
n-Propyl N-methacryloylcarbamate, colorless needles, M.P., 68°–69° C.;
Isopropyl N-methacryloylcarbamate, colorless needles; M.P., 108° C.;
n-Butyl N-methacryloylcarbamate, colorless needles; M.P., 91°–92° C.;
t-Butyl N-methacryloylcarbamate, colorless needles; M.P., 160° C.;
Stearyl N-methacryloylcarbamate, colorless needles; M.P., 38°–41° C.;
Allyl N-methacryloylcarbamate, colorless needles; M.P, 43.5° C.

Example 17

Glycidol (2.13 g; 28.8 mmol) was dissolved in dry chloroform (20 ml) under ice-cooling, and a solution of methacryloyl isocyanate (3.2 g; 28.8 mmol) in 1,2-dichloroethane (20 ml) was dropwise added thereto under nitrogen stream. After completion of the addition, chloroform and 1,2-dichloroethane were evaporated under reduced pressure to give glycidyl N-methacryloylcarbamate (5.33 g) as a viscous, colorless oil. Viscosity, 3260 cp.

Example 18

Dimethylaminoethanol (0.89 g; 10 mmol) was dissolved in dry chloroform (20 ml) under ice-cooling, and a solution of methacryloyl isocyanate (1.11 g; 10 mmol) in 1,2-dichloroethane (5 ml) was dropwise added thereto under nitrogen stream. After completion of the addition, chloroform and 1,2-dichloroethane were evaporated under reduced pressure to give dimethylaminoethyl N-methacryloylcarbamate (2.00 g), which was recrystallized from a mixture of benzene and hexane to give colorless needle-like crystals. M.P., 71°–73° C.

Examples 19 to 24

In the same manner as in Examle 18, the following compounds as shown in Table 1 were produced:

TABLE 1

$$CH_2=\underset{R}{\overset{|}{C}}-CO-NCO + HO-R^3 \longrightarrow CH_2=\underset{R}{\overset{|}{C}}-CO-NHCO-O-R^3$$

| Example No. | R | $R^3$ | Reaction Temp. (°C.) | Reaction Time (min) | M.P. (°C.) | Viscosity | Appearance |
|---|---|---|---|---|---|---|---|
| 19 | $CH_3$ | -C₆H₄-N(CH₃)₂ | 8–14 | 5 | 107–110 | — | Colorless needles |

TABLE 1-continued $$CH_2=\overset{R}{\underset{|}{C}}-CO-NCO + HO-R^3 \longrightarrow CH_2=\overset{R}{\underset{|}{C}}-CO-NHCO-O-R^3$$

| Example No. | R | R³ | Reaction Temp. (°C.) | Time (min) | M.P. (°C.) | Viscosity | Appearance |
|---|---|---|---|---|---|---|---|
| 20 | CH₃ | —CH₂CH₂—N(C₂H₅)(C₆H₅) | 2–12 | 5 | — | 4800 | Pale yellow oil |
| 21 | CH₃ | —N(piperidyl) | 13–27 | 5 | 84–86 | — | Colorless needles |
| 22 | CH₃ | —CH₂CH₂—N(morpholinyl) | 12–22 | 5 | — | 3000 | Colorless oil |
| 23 | CH₃ | —CH₂CH₂OCH₂CH₂—N(CH₃)₂ | 2–10 | 5 | — | 1140 | Colorless oil |
| 24 | CH₃ | —CH₂—CH(C₆H₅)—COO—(CH₃—N pyrrolyl) | 25–38 | 5 | — | 13700 | Colorless oil |

Example 25

To a solution of methacryloyl isocyanate (2.22 g; 20 mmol) in 1,2-dichloroethane (7.7 g), methylethylketone oxime (1.74 g; 20 mmol) was dropwise added under nitrogen stream while cooling with ice. After completion of the addition, the solvent was removed under reduced pressure to give 2-methacryloylcarbamoyloxyiminobutane (3.80 g) as a pale yellow liquid. Viscosity, 4600 cp.

Examples 26 to 31

In the same manner as in Example 25, the following compounds as shown in Table 2 were produced:

TABLE 2

$$CH_2=\overset{R}{\underset{|}{C}}-CO-NCO + HO-N=\overset{R^5}{\underset{|}{C}}-R^4 \longrightarrow CH_2=\overset{R}{\underset{|}{C}}-CO-NHCO-O-N=\overset{R^5}{\underset{|}{C}}-R^4$$

| Example No. | R | R⁴ | R⁵ | Reaction Temp. (°C.) | Time (min) | Product M.P. (°C.) | Viscosity (cp) | Appearance |
|---|---|---|---|---|---|---|---|---|
| 26 | CH₃ | H | C₆H₅ | 5–25 | 10 | 121–123 | — | Colorless needles |
| 27 | CH₃ | CH₃ | C₆H₅ | 5–25 | 10 | 74–75 | — | Colorless crystal |
| 28 | CH₃ | —(CH₂)₅— | | 12–15 | 10 | 86–88 | — | Colorless crystal |
| 29 | CH₃ | CH₃ | CH₃CO— | 12–15 | 10 | 85–87 | — | Colorless needles |
| 30 | CH₃ | CH₃ | (CH₃)₂CHCH₂— | 10–12 | 10 | — | 1400 | Colorless oil |
| 31 | CH₃ | CH₃ | H | 9–34 | 5 | — | 30 | Colorless oil |

Note:
The viscosity of the product in Example 31 was measured at 20° C.

Example 32

To a solution of methacryloyl isocyanate (4.9 g; 44 mmol) in 1,2-dichloroethane (12 ml), 2,6-di-t-butyl-4-methylphenol (50 mg) was added, and the resultant solution was ice-cooled. Methylmercaptan gas and nitrogen gas were blown into the solution. After completion of the reaction, the solvent was removed by evaporation under reduced pressure to give methyl N-methacryloylthiocarbamate (4.98 g), which was recrystallized from a mixture of hexane and benzene to give colorless prisms. M.P., 66°-68° C.

Example 33

A solution of ethanethiol (1.24 g; 20 mmol) in 1,2-dichloroethane (12 ml) was dropwise added to a solution of methacryloyl isocyanate (2.22 g; 20 mmol) in 1,2-dichloroethane (14 ml) in 10 minutes under nitrogen stream while cooling with ice. After completion of the addition, the reaction mixture was stirred for 30 minutes. The solvent was removed by evaporation under reduced pressure to give ethyl N-methacryloylthiocarbamate (2.17 g) as a pale yellow liquid. Viscosity, 150 cp.

Examples 34 to 38

In the same manner as in Example 32, the following compounds as shown in Table 3 were produced:

with ice. After completion of the addition, chloroform, 1,2-dichloroethane and methylamine were evaporated under reduced pressure to give 1-methacryloyl-3-methylurea (1.42 g), which was recrystallized from a mixture of benzene and hexane to give colorless plates. M.P., 112°-113.5° C.

Example 41

To a solution of dimethylamine (0.45 g; 10 mmol) in chloroform (20 ml), a solution of methacryloyl isocyanate (1.11 g; 10 mmol) in 1,2-dichloroethane (20 ml) was dropwise added under nitrogen stream while cooling with ice. After completion of the addition, chloroform and 1,2-dichloroethane were evaporated under reduced pressure to give 1-methacryloyl-3,3-dimethylurea (1.56 g) as a colorless oil.

IR spectrum: 3280 cm$^{-1}$ ($\gamma$NH), 1700 cm$^{-1}$ ($\gamma$C=O), 1670 cm$^{-1}$ ($\gamma$NHCO—N<), 1500 cm$^{-1}$ (amide II), 1200 cm$^{-1}$ (amide) III).

NMR $\delta$ ppm: 2.03 (methyl proton), 3.07 (methyl proton), 5.68 (vinyl proton), 6.06 (vinyl proton), 9.42 (NH proton).

TABLE 3

$$CH_2=\overset{R}{\underset{|}{C}}-CO-NCO + HS-R^3 \longrightarrow CH_2=\overset{R}{\underset{|}{C}}-CO-NHCO-S-R^3$$

| Example No. | R | R³ | Reaction Temp. (°C.) | Time (min) | Polymerization inhibitor | Product M.P. (°C.) | Viscosity (cp) | Appearance |
|---|---|---|---|---|---|---|---|---|
| 34 | CH₃ | cyclohexyl-H | −15 | −10 | 15 | Used | 81-82 | — | Colorless needles |
| 35 | CH₃ | CH₂=CHCH₂— | −8 | −3 | 15 | Used | — | 400 | Colorless oil |
| 36 | CH₃ | phenyl-CH₂— | 2 | 10 | 20 | Not used | 77-79 | — | Colorless needles |
| 37 | CH₃ | naphthyl- | 15 | 20 | 10 | Not used | 122-123 | — | Pale yellow solid |
| 38 | CH₃ | C₁₈H₃₇— | −5 | 5 | 20 | Not used | 62-64 | — | Colorless needles |

Example 39

Gaseous ammonia was blown into dry chloroform (50 g) to prepare a chloroform solution containing ammonia (0.18 g; 10.5 mmol). To the resultant solution, a solution of methacryloyl isocyanate (1.11 g; 10 mmol) in 1,2-dichloroethane (2 ml) was dropwise added under nitrogen stream while cooling with ice. After completion of the addition, chloroform and 1,2-dichloroethane were evaporated under reduced pressure to give 1-methacryloylurea (1.28 g), which was recrystallized from a mixture of benzene and hexane to give colorless needles. M.P., 137°-138° C.

Example 40

To a solution of methylamine (0.35 g; 11.29 mmol) in chloroform (30 ml), a solution of methacryloyl isocyanate (1.11 g; 10 mmol) in 1,2-dichloroethane (2 ml) was dropwise added under nitrogen stream while cooling

Examples 42 to 48

In the same manner as in Example 39, the following compounds were produced:

1-Methacryloyl-3-allylurea, colorless needles; M.P., 42°-43° C.;
1-Methacryloyl-3-(2-thiazolyl)urea, colorless needles; M.P., 166°-167° C.;
1-Methacryloyl-3,3-dicyclohexylurea, colorless prisms; M.P., 165.5°-166.5° C.;
1-Methacryloyl-3-stearylurea, colorless solid; M.P., 37.5°-40.5° C.;
1-Methacryloyl-3-phenylurea, colorless needles; M.P., 129.5°-131.° C.;
1-Methacryloyl-3-benzylurea, colorless needles; M.P., 96.5°-98° C.;
N-Methacryloylmorpholinecarboxamide, colorless prisms; M.P., 104°-105° C.

Example 49

To a solution of acetamide (0.59 g; 10 mmol) in 1,2-dichloroethane (20 ml), a solution of methacryloyl isocyanate (1.11 g; 10 mmol) in 1,2-dichloroethane (5 ml) was dropwise added at room temperature, and the reaction mixture was stirred at 80° C. for 3.5 hours. After cooling, 1,2-dichloroethane was evaporated under reduced pressure to give 1-methacryloyl-3-acetylurea (1.63 g), which was recrystallized from a mixture of benzene and hexane to give colorless needles. M.P., 92°–94° C.

Example 50

To a solution of acetamide (0.59 g; 10 mmol) in 1,2-dichloroethane (20 ml), a solution of methacryloyl isocyanate (1.11 g; 10 mmol) in 1,2-dichloroethane (10 ml) was dropwise added. After completion of the addition, pyridine (5 drops) was added to the solution, and then stirring was continued at room temperature for 12 hours. 1,2-Dichloroethane was evaporated under reduced pressure to give 1-methacryloyl-3-acetylurea (1.36 g), which was recrystallized from a mixture of benzene and hexane to give colorless needles. M.P., 92°–94° C.

Examples 51 to 57

In the same manner as in Example 49, the following compounds as shown in Table 4 were produced:

Example 58

To a solution of propyleneimine (0.57 g; 10 mmol) in chloroform (20 ml), a solution of methacryloyl isocyanate (1.11 g; 10 mmol) in 1,2-dichloroethane (5 ml) was dropwise added under nitrogen stream while cooling with ice. After completion of the addition, chloroform and 1,2-dichloroethane were evaporated under reduced pressure to give N-methacryloylcarbamoylpropyleneimine (1.68 g). Viscosity, 1100 cp.

Example 59

In the same manner as in Example 58 but using ethyleneimine in place of propyleneimine, there was produced N-metacryloylcarbamoylethyleneimine.

Example 60

A solution of metacryloyl isocyanate (11.1 g; 100 mmol) in dichloroethane (22 g) and methyl p-hydroxybenzoic acid (15.0 g; 100 mmol) were added to benzene (30 g), and the resultant mixture was heated at 80° C. under reflux for 60 minutes. The solvent was removed by evaporation under reduced pressure to give p-methoxycarbonylphenyl N-methacryloylcarbamate as crude crystals. Recrystallization from a mixture of hexane and chloroform gave colorless prisms. M.P., 98°–100° C.

Examples 61 to 68

TABLE 4

$$CH_2=\overset{R}{\underset{|}{C}}-CO-NCO + H-\overset{R^{10}}{\underset{|}{N}}-CO-R^9 \longrightarrow$$

$$CH_2=\overset{R}{\underset{|}{C}}-CO-NHCO-\overset{R^{10}}{\underset{|}{N}}-CO-R^9$$

| Example No. | R | R⁹ | R¹⁰ | Reaction Temp. (°C.) | Reaction Time (hr) | M.P. (°C.) | Appearance |
|---|---|---|---|---|---|---|---|
| 51 | CH₃ | —C₆H₅ | H | 80 | 2.5 | 160–161 | Colorless needles |
| 52 | CH₃ | —CH₂—C₆H₅ | H | 85 | 3.5 | 115–117 | Colorless needles |
| 53 | CH₃ | CH₂=C(CH₃)— | H | 85 | 2.0 | 130–132 | Colorless needles |
| 54 | CH₃ | C₁₈H₃₇— | H | 85 | 2.0 | 86–88 | Colorless solid |
| 55 | CH₃ | —(CH₂)₅— | | 75 | 0.5 | 89–91 | Colorless needles |
| 56 | CH₃ | —(CH₂)₃— | | 85 | 1.0 | 106–107 | Colorless needles |
| 57 | CH₃ | H | H | 83 | 2.0 | 102–104 | Colorless needles |

In the same manner as in Example 60, the following compounds as shown in Table 5 were produced:

TABLE 5

| Example No. | Blocking agent | Reaction Temp. (°C.) | Reaction Time (min) | Product Appearance | M.P. (°C.) |
|---|---|---|---|---|---|
| 61 | 2,6-di-t-Butyl-p-cresol | 80 | 30 | Colorless prisms | 143–145 |
| 62 | 1-Methoxy-2-propanol | −20~0 | 15 | Colorless needles | 84–86 |
| 63 | 2-Methyl-1-butanol | 15~20 | 10 | White solid | 41–43 |

TABLE 5-continued

| Example No. | Blocking agent | Reaction Temp. (°C.) | Time (min) | Product Appearance | M.P. (°C.) |
|---|---|---|---|---|---|
| 64 | Acetone oxime | 15~20 | 30 | White wax-like solid | 31–32 |
| 65 | N-Hydroxysuccinimide | 80 | 30 | Colorless needles | 119–112 |
| 66 | 1,2,3-Benzotriazole | 20~35 | 30 | Colorless needles | 71.5–72.5 |
| 67 | 2-Ethylhexanol | 15~20 | 10 | Colorless oil (viscosity, 800 cp) | |
| 68 | Imidazole | 15~20 | 10 | | |

Examples 69 and 70

To a solution of acryloyl isocyanate (9.7 g; 100 mmol) in dichloroethane (20 g), a solution of t-butanol (7.4 g; 100 mmol) in dichloroethane (20 g) was dropwise added under ice-cooling in 5 minutes. The solvent was removed by evaporation under reduced pressure to give t-butyl N-acryloylcarbamate as crude crystals, which were recrystallized from chloroform to give colorless needles. M.P., 131°–132° C.

In the same manner as above but using 2,6-di-t-butyl-4-methylphenol, there was produced 2,6-di-t-butyl-4-methylphenyl N-aclyloylcarbamate as colorless needles. M.P., 150°–151° C.

Example 71

To methacryloyl isocyanate (5.55 g; 50 mmol) in dichloroethane (15 ml), a solution of o-fluoroaniline (5.55 g; 50 mmol) in chloroform (30 ml) was dropwise added. After completion of the addition, the precipitated crystals were collected by filtration. From the filtrate, the solvent was removed by evaporation under reduced pressure. The residue and the crystals were cobmined together and recrystallized from benzene to give N-methacryloyl-N'-o-fluorophenylurea as colorless needles. M.P., 155°–157° C.

Examples 72 to 74

In the same manner as in Example 71, the following compounds as shown in Table 6 were produced:

TABLE 6

$$CH_2=\overset{R}{\underset{|}{C}}-CO-NCO + H-Rf \longrightarrow CH_2=\overset{R}{\underset{|}{C}}-CO-NHCO-Rf$$

| Example No. | R | Rf | Reaction Temp. (°C.) | Time (min) | Product M.P. (°C.) | Appearance |
|---|---|---|---|---|---|---|
| 72 | $CH_3$ | 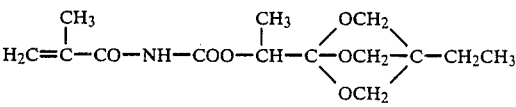 | 16–18 | 60 | 155–156 | Colorless prisms |
| 73 | $CH_3$ | $(CF_3)_2CHO-$ | 10–15 | 120 | 112.5–113 | Colorless needles |
| 74 | $CH_3$ | $CF_3(CF_2)_6CH_2O-$ | 20–25 | 240 | 72–73 | Colorless plates |

Example 75

To a solution of methacryloyl isocyanate (8.33 g; 0.075 mmol) in dichloroethane (3 g), a solution of butylated melamine ("Cymel C-1156" manufactured by American Cyanamid Co.; molecular weight, 990) (35.2 g; 0.036 mol) in dichloroethane (70 g) was dropwise added under cooling with ice. After completion of the addition, the resultant mixture was stirred at room temperature for 20 hours. Dichloroethane and methacryloyl isocyanate were removed by evaporation under reduced pressure. The residue was dried in vacuo to give the methacryloyl isocyanate-butylated melamine adduct as a colorless oil. Molecular weight, 1160 (determined by the GPC method). Viscosity, 23,000 cp.

Example 76

Into a 100 ml volume three-necked flask equipped with a stirrer, a thermometer, a nitrogen introducing pipe and a cooler, there were charged 4-methyl-1-(alpha-hydroxyethyl)-2,6,7-trioxabicyclo[2.2.2]octane (5.64 g; 30 mmol) and 1,2-dichloroethane (60 ml), and the resultant mixture was stirred at room temperature. Methacryloyl isocyanate (3.33 g; 30 mmol) was dropwise added thereto in 5 minutes, and the resulting mixture was stirred at room temperature for 2 hours. The solvent was evaporated, and the residue was recrystallized from a small amount of tetrahydrofuran to give a compound of the formula:

$$H_2C=\overset{CH_3}{\underset{|}{C}}-CO-NH-COO-\overset{CH_3}{\underset{|}{CH}}-\overset{}{\underset{}{C}}\begin{pmatrix}OCH_2\\OCH_2\\OCH_2\end{pmatrix}C-CH_2CH_3$$

as colorless needles (8.0 g). M.P., 146°–148° C.

Example 77

Into the same flask as in Example 76, there were charged 1-ethyl-4-hydroxymethyl-2,6,7-trioxabicyclo[2.2.2]-octane (5.28 g; 30 mmol) and 1,2-dichloroethane (60 ml), and the resultant mixture was stirred at room temperature. Methacryloyl isocyanate (3.33 g; 30 mmol) was dropwise added thereto in 5 minutes, and the resulting mixture was stirred at room temperature for 2 hours. The solvent was evaporated, and the residue was purified by silica gel column chromatography using a mixture of tetrahydrofuran and hexane as an eluent to obtain a compound of the formula:

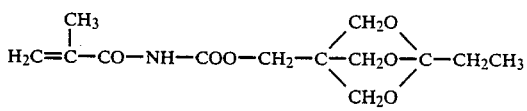

as crystals (5.6 g). M.P., 106°–109° C.

Example 78

Into the same flask as in Example 76, there were charged 2-hydroxymethyl-1,4,6-trioxaspiro[4.4]nonane (4.8 g; 30 mmol) and 1,2-dichloroethane (60 ml), and the resultant mixture was stirred at room temperature. Methacryloyl isocyanate (3.33 g; 30 mmol) was dropwise added thereto in 5 minutes, and the resulting mixture was stirred at room temperature for 2 hours. The solvent was evaporated, and the residue was purified by active alumina column chromatography using a mixture of hexane and chloroform as an eluent to obtain a compound of the formula:

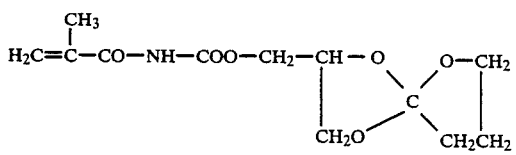

as a colorless transparent, viscous liquid.

Example 79

Into a three-necked flask purged with nitrogen gas, benzoin (2.12 g; 10 mmol) was charged, and chloroform (30 ml) was added thereto. To the resultant solution, a solution of methacryloyl isocyanate (1.11 g; 10 mmol) in 1,2-dichloroethane (7 g) was dropwise added in 5 minutes under nitrogen stream while stirring. Chloroform and 1,2-dichloroethane were removed by evaporation under reduced pressure to give benzoylbenzyl N-methacryloylcarbamate (3.3 g), which was recrysallized from a mixture of benzene and chloroform to give colorless transparent plates. M.P., 161°–163° C.

Example 80

Into a three-necked flask purged with nitrogen gas, p-hydroxybenzophenone (1.98 g; 10 mmol) was charged, and chloroform (10 ml) was added thereto. To the resultant solution, a solution of methacryloyl isocyanate (1.11 g; 10 mmol) in 1,2-dichloroethane (5 ml) was dropwise added in 5 minutes under nitrogen stream while stirring. Chloroform and 1,2-dichloroethane were removed by evaporation under reduced pressure to give p-benzoylphenyl N-methacryloylcarbamate (3.1 g), which was recrysallized from a mixture of benzene and chloroform to give white granules. M.P., 96°–97° C.

Example 81

Into a three-necked flask purged with nitrogen gas, methacryloyl isocyanate (1.11 g; 10 mmol) was charged, and 1,2-dichloroethane (20 ml) was added thereto. A solution of cinnamyl alcohol (1.34 g) in 1,2-dichloroethane (20 ml) was dropwise added thereto under nitrogen stream in 10 minutes while stirring. 1,2-Dichloroethane was removed by evaporation under reduced pressure to give cinnamyl N-methacryloylcarbamate (2.4 g), which was washed with hexane and purified by silica gel column chromatography to give colorless needles. M.P., 66°–67° C.

Examples 82 and 83

To beta-chloropropionyl isocyanate (13.3 g; 100 mmol) in dichloroethane (20 g), a solution of t-butanol (7.4 g; 100 mmol) in dichloroethane (20 g) was dropwise added under ice-cooling in 5 minutes, whereby t-butyl beta-chloropropionylcarbamate was produced. Triethylamine (9.8 g; 100 mmol) was added to the reaction mixture, and the resultant mixture was stirred for 60 minutes. Precipitated salts were eliminated by filtration, and the filtrate was concentrated under reduced pressure to give t-butyl acryloylcarbamate as crude crystals, which were recrystallized from chloroform to give colorless needles. M.P., 131°–132° C.

In the same manner as above but using 2,6-di-t-butyl-4-methylphenol in place of t-butanol, there was prepared 2,6-di-t-butyl-4-methylphenyl acryloylcarbamate as colorless needles. M.P., 150°–151° C.

Example 84

To a solution of beta-chloroisobutyryl isocyanate (7.38 g; 50 mmol) in chloroform (50 ml), a solution of 1,1,1,3,3,3-hexafluoroisopropanol (8.4 g; 50 mmol) in chloroform (10 ml) was dropwise added at 10° C. under ice-cooling. After completion of the addition, the resultant mixture was stirred for 1 hour, whereby hexafluoroisopropyl beta-chloroisobutyrylcarbamate was produced. A solution of triethylamine (5.05 g; 50 mmol) in chloroform (50 ml) was added to the reaction mixture in 30 minutes under ice-cooling. The reaction mixture was stirred for 1 hour, and precipitated triethylamine hydrochloride (6.87 g) was eliminated by filtration. The filtrate was concentrated under reduced pressure to give hexafluoroisopropyl N-methacryloylcarbamate (13.4 g), which was recrystallized from benzene to give colorless prisms. M.P., 112.5°–113° C.

Example 85

To a solution of beta-chloriosobutyryl isocyanate (5.31 g; 0.036 mmol) in chloroform (50 ml), a solution of butylated melamine ("Cymel C-1156" manufactured by American Cyanamid Co.; molecular weight, 990) (35.2 g; 0.036 mmol) in chloroform (50 ml) was added under ice-cooling. After completion of the addition, the resultant mixture was stirred at room temperature for 4 hours. Precipitated triethylamine hydrochloride (4.95 g) was eliminated by filtration. The filtrate was concentrated under reduced pressure to give the methacryloyl isocyanate-butylated melamine adduct as a colorless oil. Molecular weight, 1180 (determined by the GPC method). Viscosity, 23,400 cp.

Reference Example 1

To a mixture of butyl acetate (8.0 g) and toluene (4.0 g) kept at 100° C, a mixture of methacryloyl isocyanate (4.0 g; 0.036 mol), 2-ethylhexyl acrylate (4.0 g), styrene (4.0 g) and 2,2′-azobis(2,4-dimethylvaleronitrile) (0.36 g) was dropwise added in 2 hours. After completion of the addition, a solution of 2,2′-azobis(2,4-dimethylvaleronitrile) (0.06 g) in toluene (3.0 g) was added thereto in 20 minutes, and the resultant mixture was aged for 50 minutes. The reaction mixture was then cooled to 35° C., and a solution of cinnamyl alcohol (4.9 g; 0.036 mol) in butyl acetate (5.0 g) was dropwise added thereto in 20 minutes. Addition of acetone (40.0 g) gave a yellowish milky solution comprising a copolymer having the molecule of cinnamyl alcohol added to the pendant isocyanate group. Non-volatile content, 20.3 %. Number average molecular weight, 4591. [α] = 1.88.

The copolymer solution was coated on a glass plate by the aid of 100 μ doctor's plate and allowed to stand at room temperature for 12 hours for drying to give a film of 10 μ in thickness. The thus obtained film was passed through a ultraviolet ray irradiation apparatus (manufactured by Japan Storage Battery Co., Ltd.; output, 80 W/cm; ozone generation type; line speed, 1 m/min per 1 pass). The hardening extent was evaluated by acetone rubbing, and the results were as follows:

|  | Peeling off |
| --- | --- |
| Before irradiation | 6 times |
| After irradiation | 28 times |

Reference Example 2

To butyl acetate (8.0 g) kept at 100° C, a mixture of methacryloyl isocyanate (2.0 g), 2-ethylhexyl acrylate (4.0 g), styrene (8.0 g) and 2,2'-azobis(2,4-dimethylvaleronitrile) (0.36 g) was dropwise added in 2 hours. After completion of the addition, a solution of 2,2'-azobis(2,4-dimethylvaleronitrile) (0.06 g) in toluene (3.0 g) was added thereto in 20 minutes, and the resultant mixture was aged for 30 minutes. The reaction mixture was then cooled to 35° C., and a solution of benzoin (3.8 g) in dioxane (40.0 g) was dropwise added thereto in 20 minutes. After aging for 30 minutes, there was produced a copolymer solution having a non-volatile content of 22.6 %. The copolymer solution thus obtained was treated with hexane to give a copolymer having the molecule of benzoin added to the pendant isocyanate group as a prism-like solid. Number average molecular weight, 7884. [α] = 1.86.

The copolymer solution was coated on a glass plate by the aid of 100 u doctor's plate and allowed to stand at room temperature for 12 hours for drying to give a film of 10μ in thickness. The thus obtained film was passed through a ultraviolet ray irradiation apparatus (manufactured by Japan Storage Battery Co., Ltd.; output, 80 W/cm; ozone generation type; line speed, 1 m/min per 1 pass). The hardening extent was evaluated by acetone rubbing, and the results were as follows:

|  | Peeling off |
| --- | --- |
| Before irradiation | 6 times |
| After irradiation | 22 times |

Reference Example 3

Preparation of the polymer:

In a reactor, a solution of the monomer (2) as shown in Table 7 in n-butanol (30 parts) was charged, and the monomers (1) as shown in Table 7 and xylene (50 parts) were added thereto. The content in the reactor was heated up to 120° C., and a solution of t-butylperoxy-2-ethylhexanoate (0.7 part) in xylene (20 parts) was dropwise added thereto over a period of 3 hours while stirring and allowed to stand at 120° C. for 3 hours, during which the polymerization proceeded.

The reaction mixture comprising the polymer was subjected to measurement of the non-volatile content, the viscosity (Gardner bubble viscosity) and the number average molecular weight. Also, the tensile test and the tape peeling off test were carried out in the following manner:

Tensile test:

The reaction mixture containing the polymer was admixed with a melamine resin ("Super-Beckamine L-117-60" manufactured by Dainippon Ink Co., Ltd.) in a weight proportion of 8:2 (in terms of solid content). The resultant mixture was applied onto the surface of a polypropylene plate by the aid of a film applicator, followed by baking at 120° C. for 30 minutes to give a coating film of 100 μ in thickness. The coating film was cut off to obtain a test piece of 5 cm × 1 cm, and the test piece was stretched by the aid of a tensile test machine with a pulling rate of 5 mm/minute at a temperature of 20° C. or −20° C.

Cross cut tape peeling off test:

The reaction mixture containing the polymer was admixed with a melamine resin in the same manner as above. The resultant mixture was applied onto a steel plate by the aid of a film applicator and set for 5 minutes, followed by backing at 120° C. for 30 minutes to give a coating film of 40 u. The coating film was cut to make 11 lines in parallel with intervals of 1 mm in the machine direction and 11 lines in parallel with intervals of 1 mm in the transverse direction so that 100 squares were formed in an area of 1 cm². An adhesive polyester tape cut in about 75 mm was firmly and flatly sticked on said squares with a pressure of finger and then peeled off.

The results are shown in Table 7.

TABLE 7

|  |  |  | A | B | C | D | E |
| --- | --- | --- | --- | --- | --- | --- | --- |
| Co-poly-mer | Monomers (1) | Ethayl acrylate | 40.23 | 40.23 | 40.23 | 40.23 | 40.23 |
|  |  | n-Butyl acrylate | 16.60 | 16.60 | 16.60 | 16.60 | 16.60 |
|  |  | Styrene | 5.0 | 5.0 | 5.0 | 5.0 | 5.0 |
|  |  | Methacrylic acid | 2.30 | 2.30 | 2.30 | 2.30 | 2.30 |
|  |  | Hydroxyethyl acrylate | 13.45 | 13.45 | 13.45 | 13.45 | 13.45 |
|  | Monomers (2) | Methyl methacrylate | 22.41 | 17.41 | 12.41 | 14.91 | 19.91 |
|  |  | N-Methacryloyl-N'-methyl urea | — | 5.0 | — | — | — |
|  |  | N-Methacryloyl-N'-acetyl urea | — | — | 10.0 | — | — |
|  |  | Dimethylaminoethyl N-methacryloylcarbamate | — | — | — | 7.5 | — |
|  |  | Ethyl N-methacryloyl-carbamate | — | — | — | — | 2.5 |

TABLE 7-continued

|  |  |  | A | B | C | D | E |
|---|---|---|---|---|---|---|---|
|  | NV/Viscosity |  | 50/R<<S | 50/S<T | 50/U | 50/T<U | 50/T |
|  | Number average molecular weight |  | 16000 | 16000 | 15000 | 18000 | 17000 |
| Tensile test | 20° C. | Young's modulus (kg/cm$^2$) | 734 | 966 | 929 | 1068 | 1007 |
|  |  | Tensile strength (kg/cm$^2$) | 76 | 92 | 89 | 105 | 98 |
|  |  | Elongation (%) | 62.8 | 85.3 | 77.5 | 92.1 | 90.4 |
|  | −20° C. | Young's modulus (kg/cm$^2$) | 14900 | 15800 | 15400 | 16200 | 15900 |
|  |  | Tensile strength (kg/cm$^2$) | 417 | 488 | 456 | 518 | 505 |
|  |  | Elongation (%) | 9.3 | 14.2 | 12.9 | 18.0 | 16.8 |
| Tape peeling off test (cross cut) |  |  | 87/100 | 100/100 | 99/100 | 100/100 | 100/100 |

Reference Example 4

Preparation of the polymer:

In a reactor, a solution of the monomer (2) as shown in Table 8 in n-butanol (30 parts) was charged, and the monomers (1) as shown in Table 8 and xylene (50 parts) were added thereto. The content in the reactor was heated up to 120° C., and a solution of azobisisobutyronitrile (0.8 part) in xylene (20 parts) was dropwise added thereto over a period of 5 hours while stirring, during which the polymerization proceeded.

The reaction mixture comprising the polymer was subjected to measurement of the non-volatile content, the viscosity (Gardner bubble viscosity) and the number average molecular weight. Also, the pigment as shown in Table 8 (25 parts) was added to the reaction mixture (100 parts) comprising the resinous polymer (50 parts), and the resultant mixture was stirred well. Macroscopic observation was made on the dispersibility of the pigment.

The results are shown in Table 8.

TABLE 8

|  |  |  | A | B | C | D | E | F |
|---|---|---|---|---|---|---|---|---|
| Copolymer | Monomers (1) | Styrene | 30 | 30 | 30 | 30 | 30 | 30 |
|  |  | Methyl methacrylate | 30 | 30 | 30 | 30 | 30 | 30 |
|  |  | n-Butyl acrylate | 40 | 40 | 40 | 40 | 40 | 40 |
|  | Monomers (2) | Methacrylic acid | — | 2 | — | — | — | 2 |
|  |  | Methyl N-methacryloylcarbamate | — | — | 2 | — | — | — |
|  |  | Dimethylaminoethoxyethyl N-methacryloylcarbamate | — | — | — | 10 | — | — |
|  |  | N-Methacryloyl-N'-phenylacetylurea | — | — | — | — | 20 | — |
|  |  | N-Methacryloylmorpholine-carboxamide | — | — | — | — | — | 4 |
|  | NV/Viscosity |  | 50/N<0 | 50/N<0 | 50/N<0 | 50/0 | 50/0<P | 50/N<<0 |
|  | Mn |  | 15000 | 14000 | 14000 | 15000 | 16000 | 15000 |
| Dispersibility | Titanium oxide ("CR-95" manufactured by Ishhara Sangyo) |  | X | O | O | O | O | O |
|  | Carbon black ("MA-100" manufactured by Mitsubishi Chemical) |  | X | X | O | O | O | O |
|  | Phthalocyanine blue ("FASTGEN BLUE NK" manufactured by Dai-Nippon Ink Chemical) |  | X | Δ | O | O | O | O |
|  | Quinacridone red ("CYNQUASHA RED RT-759D" manufactured by DuPont) |  | X | X | O | O | O | O |

Note: X, poor; Δ, good; O excellent.

What is claimed is:

1. An alkenoylcarbamate compound of the formula:

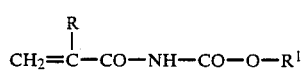
(I-1)

wherein R is hydrogen or lower alkyl and R$^1$ is stearyl, lower alkenyl, or phenyl.

2. The alkenoylcarbamate compound according to claim 1, wherein R is hydrogen and R$^1$ is stearyl, lower alkenyl, phenyl(lower)alkyl or phenyl.

3. An alkenoylcarbamate compound of the formula:

$$CH_2=\overset{R}{\underset{|}{C}}-CO-NH-CO-O-R^2 \qquad (I-2)$$

wherein R is lower alkyl and R$^2$ is glycidyl or glycidyloxy(lower)alkyl.

4. An alkenoylcarbamate compound of the formula:

$$CH_2=\overset{R}{\underset{|}{C}}-CO-NH-CO-O-R^3 \qquad (I-3)$$

wherein R is hydrogen or lower alkyl and R$^3$ is di(lower)-alkylamino(lower)alkyl, di(lower)alkylaminophenyl, lower alkylphenylamino(lower)alkyl, lower alkyl-phenyl(lower)-alkylamino(lower)alkyl, pyrrolidino, piperidino, morpholino, pyrrolidino(lower)alkyl, piperidino(lower)alkyl, morpholino(lower)alkyl, di(lower)alkylamino(lower)alkoxy(lower)alkyl or 2-(8-methyl-8-azabicyclo{3.2.1}oct-3-yloxycarbonyl)-2-phenylethyl.

5. An alkenoylcarbamate compound of the formula:

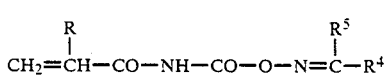
(I-4)

wherein R is hydrogen or lower alkyl and R⁴ and R⁵ are each hydrogen, lower alkyl, lower alkenyl, phenyl(lower)alkyl, phenyl or lower alkanoyl, or R⁴ and R⁵ are taken together to form a lower alkylene chain.

6. An alkenoylcarbamate compound of the formula:

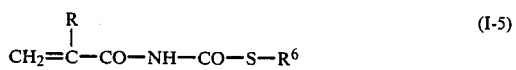

(I-5)

wherein R is hydrogen or lower alkyl and R⁶ is lower alkyl, stearyl, cyclo(lower)alkyl, lower alkenyl, phenyl(lower)alkyl, phenyl or nephthyl.

7. An alkenoylcarbamate compound of the formula:

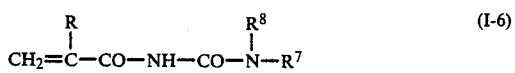

(I-6)

wherein R is hydrogen or lower alkyl and R⁷ and R⁸ are each hydrogen, lower alkyl, stearyl, cyclo(lower)alkyl, lower alkenyl, phenyl(lower)alkyl, phenyl or thiazolyl, or R⁷ and R⁸ are taken together with the nitrogen atom to which they are attached to form a morpholino group.

8. An alkenoylcarbamate compound of the formula:

(I-7)

wherein R is hydrogen or lower alkyl, R⁹ is hydrogen, alkyl of not more than 18 carbon atoms, lower alkenyl, phenyl or phenyl(lower)alkyl and R¹⁰ is hydrogen, or R⁹ and R¹⁰ are taken together to form a lower alkylene chain, provided that when R is hydrogen, R⁹ is not lower alkenyl.

9. An alkenoylcarbamate compound of the formula:

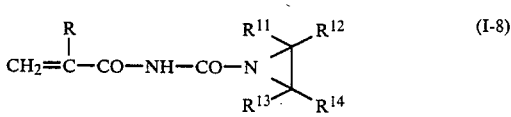

(I-8)

wherein R, R¹¹, R¹², R¹³ and R¹⁴ are each hydrogen or lower alkyl.

10. The alkenoylcarbamate compound according to claim 9, wherein R is lower alkyl and R¹¹, R¹², R¹³ and R¹⁴ are each hydrogen.

11. The alkenoylcarbamate compound according to claim 9, wherein R and R¹¹ are each lower alkyl and R¹², R¹³ and R¹⁴ are each hydrogen.

12. An alkenoylcarbamate compound of the formula:

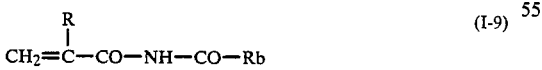

(I-9)

wherein R is hydrogen or lower alkyl and Rb is a blocking group effected by excluding an active hydrogen atom from etherified alcohols, aromatic alcohols, active methylene compounds, lactams, N-hydroxyimides, oximes, imidazoles, triazoles or amines.

13. The alkenoylcarbamate compound according to claim 12, wherein the blocking group is effected by excluding an active hydrogen atom from methyl 4-hydroxybenzoate, 2,6-di-t-butyl-p-cresol, 1-methoxy-2-propanol, 2-methyl-1-butanol, acetone oxime, N-hydroxysuccinimide, 1,2,3-benzotriazole, 2-ethylhexanol or imidazole.

14. An alkenoylcarbamate compound of the formula:

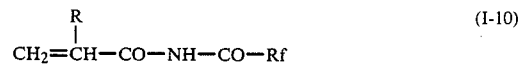

(I-10)

wherein R is hydrogen or lower alkyl and Rf is a fluorine atom-containing group effected by excluding an active hydrogen atom from 1,1,1,3,3,3-hexafluoroisopropanol, o-aminobenzotrifluoride, m-aminobenzotrifluoride, p-aminobenzotrifluoride, 2-amino-5-bromobenzotrifluoride, 3-amino-4-bromobenzotrifluoride, 5 amino-2-bromotrifluoride, 2-amino-5-chlorobenzotrifluoride, 3-amino-4-chlorobenzotrifluoride, 5-amino-2- chlorobenzotrifluoride, 2 amino-5-fluorobenzotrifluoride, 3-amino-4-fluorobenzotrifluoride, 5-amino-2-fluorobenzotrifluoride, 3-amino-5-methoxybenzotrifluoride, 2-amino-5-nitrobenzo-trifluoride, 4-amino 3-nitrobenzotrifluoride, 5-amino-2-nitrobenzotrifluoride, 4 amino-2,3,5,6-tetrafluorobenzamide, 4-amino-2,3,5,6-tetrafluorobenzoic acid, 4-amino-2,3,5,6-tetrafluorobenzonitrile, bis(trifluoromethylacetamide), chlorodifluoroacetamide, chlorodifluoroacetic acid, 3-chloro-4-fluoroaniline 2-chloro-6-fluorobenzoic acid, 3-chloro-4-fluorobenzoic acid, 2-chloro-6-fluorobenzyl alcohol, 2-chloro-4-fluorophenol, 2-chloro-6-fluorophenylacetic acid, 1-chloro-3-fluoro-2-propanol, 4 chloro-3-hydroxybenzotrifluoride, decafluorobenzhydrol, 3,4-diaminobenzotrifluoride, 3,5-diaminobenzotrifluoride, 4,4,-diamino-octafluorobiphenyl, 1,3-dichlorotetrafluoroisopropanol, difluoroacetic acid, 2,4-difluoroaniline, 2,5-difluoroaniline, 2,6-difluoroaniline, 2,4-difluorobenzamide, 2,5-difluorobenzamide, 2,6-difluorobenzamide, 3,4-difluorobenzamide, 2,4-difluorobenzoic acid, 2,5-difluorobenzoic acid, 2,6-difluorobenzoic acid, 3,4-difluorobenzoic acid or 1H,1H-oentadecafluorooctanol.

15. An alkenoylcarbamate compound of the formula:

$$CH_2=\overset{R}{\underset{|}{C}}-CO-NH-CO-Rm$$

(I-11)

wherein R is hydrogen or lower alkyl and Rm is a triazine skeleton-containing group effected by excluding an active hydrogen atom from melamine, methylolated melamines, lower alkoxymethyloimelamines or guanamines.

16. An alkenoylcarbamate compound of the formula:

$$CH_2=\overset{R}{\underset{|}{C}}-CO-NH-CO-Rnc$$

(I-12)

wherein R is hydrogen or lower alkyl and Rnc is a non-contractive structure-containing group effected by excluding an active hydrogen atom from the compounds of the formulas:

$$HO-\underset{R^{15}}{\overset{|}{C}H}-C\underset{\diagdown CH_2O\diagup}{\overset{\diagup CH_2O\diagdown}{\underset{}{-}}}C-R^{16}$$

(III-a)

-continued

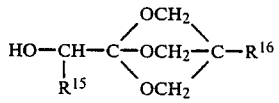
(III-b)

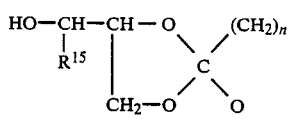
(III-c)

wherein $R^{15}$ and $R^{16}$ are each hydrogen or lower alkyl and n is an integer of 3 to 5.

17. The alkenoylcarbamate compound according to claim 16, wherein the non-contractive structure-containing group is effected by excluding an active hydrogen atom from 1 methyl-4-hydroxymethyl-2,6,7-trioxabicyclo{2.2.2}-octane, 1-ethyl-4-hydroxymethyl-2,6,7-trioxabicyclo{2.2.2}octane, 4-ethyl-1-hydroxymethyl-2,6,7-trioxabicyclo{2.2.2}octane, 2-hydroxymethyl-1,4,6-trioxaspiro{4.4}nonane, 2-hydroxymethyl-1,4,6-trioxaspiro{4.6}decane, 2-hydroxymethyl-1,4,6-trioxaspiro{ 4.6}undecane, 4-methyl-1-(alpha-hydroxyethyl)-2,6,7-trioxabicyclo{2.2.2}octane or 4-ethyl-1-(alphahydroxyethyl)-2,6,7-trioxabicyclo{2.2.2}octane.

18. An alkenoylcarbamate compound of the formula:

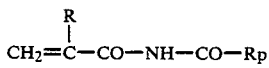
(I-13)

wherein R is hydrogen or lower alkyl and Rp is a photosensitive group or structure effected by excluding an active hydrogen atom from an olefin, cinnamoyl, cinnamylidene, cinnamylideacetyl, furylacryloyl, coumarine, pyron, benzalacetophenone, styrilpyridine, anthracene, stilben, alpha-phenylmaleimide, azide, phenylazide, sulfonylazide, carbonylazide, diazo, alphaquinonediazide benzophenone, benzoin, 1,3-dioxane, dithiocarbamate, xanthete, 1,2,3-thiadiazole, cyclopropene, azadioxabicyclo or spiropyran.

19. The alkenoylcarbamate compound according to claim 18, wherein the photosensitive group or structure is effected by excluding an active hydrogen atom from benzoin, acetoin, p-hydroxybenzaldehyde, p-hydroxybenzophenone, 1,4,9,10-tetrahydroxyanthracene, benzohydrol, ascorbic acid, cinnamyl alcohol, benzylic acid, 4-methoxyphenol, p-nitrophenol, 2-mercaptobenzothiazole, p-aminoacetophenone, thiocyanamine, alcohols, thiols, carboxylic acids, thiocarboxylic acid, benzophenone, acetophenone, 9-fluoresoneacetophenone, alpha-benzoylbenzoic acid, benzylphenyl ketone, propiophenone, benzalacetophenone, benzoylacetone or benzaldehyde.

20. An alkenoylcarbamate compound of the formula:

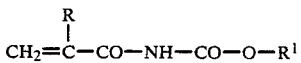
(I-1)

wherein R is methyl and $R^1$ is stearyl, lower alkenyl or phenyl.

* * * * *